(12) United States Patent
Mimura et al.

(10) Patent No.: US 8,524,153 B2
(45) Date of Patent: Sep. 3, 2013

(54) QUALITY CONTROL SYSTEM

(75) Inventors: Tomonori Mimura, Kasama (JP);
Kazumitsu Kawase, Ichinomiya (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1054 days.

(21) Appl. No.: 11/710,424

(22) Filed: Feb. 26, 2007

(65) Prior Publication Data

US 2007/0217949 A1 Sep. 20, 2007

(30) Foreign Application Priority Data

Mar. 14, 2006 (JP) ................... 2006-068481

(51) Int. Cl.
*G01N 21/00* (2006.01)

(52) U.S. Cl.
USPC ........... 422/63; 422/62; 422/65; 422/66; 422/67; 702/81; 702/179; 436/43; 436/47; 436/50; 436/180; 700/79; 700/81; 700/83; 700/34; 700/266; 700/281

(58) Field of Classification Search
USPC ........... 422/62, 63, 67; 702/81, 179; 436/43, 436/47, 50, 180; 700/79, 81, 83, 34, 266, 700/281
See application file for complete search history.

(56) References Cited

U.S. PATENT DOCUMENTS

| | | | |
|---|---|---|---|
| 5,150,289 A * | 9/1992 | Badavas | 700/34 |
| 5,616,504 A | 4/1997 | Brown et al. | |
| 5,835,384 A | 11/1998 | Lin | |
| 6,295,506 B1 * | 9/2001 | Heinonen et al. | 702/104 |
| 6,579,717 B1 * | 6/2003 | Matsubara et al. | 436/50 |
| 6,846,457 B1 * | 1/2005 | Tokiwa et al. | 422/67 |
| 2004/0220761 A1 | 11/2004 | Yundt-Pacheco | |

FOREIGN PATENT DOCUMENTS

| | | |
|---|---|---|
| EP | 0871034 A2 | 10/1998 |
| EP | 1061372 A2 | 12/2000 |
| EP | 1260818 A1 | 11/2002 |
| EP | 1772736 A1 | 4/2007 |
| JP | 2003-004750 | 1/2003 |
| WO | 02/052278 A1 | 7/2002 |
| WO | 2006009251 A1 | 1/2006 |

OTHER PUBLICATIONS

European Search Report received in EP Application No. 07003784 dated Jan. 21, 2013.

* cited by examiner

*Primary Examiner* — Jyoti Nagpaul
(74) *Attorney, Agent, or Firm* — Mattingly & Malur, PC

(57) ABSTRACT

In a clinical laboratory of a hospital, an enormous amount of effort has been required to maintain the quality of an analyzer, standard solution and control samples. An object of the present invention is to provide a control method for controlling a clinical laboratory with reduced cost, and a control apparatus using the same.

In order to control data of an analyzer, standard solution, and a control sample, a support center is connected to each analyzer located in each hospital through a network line. Various kinds of analysis parameters and the result of measurements are exchanged so as to provide each clinical laboratory with a control situation in real time.

20 Claims, 7 Drawing Sheets

QUALITY CONTROL SYSTEM

BACKGROUND OF THE INVENTION

1. Field of the Invention

The present invention relates to a quality control system for use in an automated analyzer for analyzing components contained in a biological sample, and more particularly to a quality control system that uses the result of measuring a standard solution.

2. Description of the Related Art

An automated analyzer used for clinical laboratory tests measures patients/samples to analyze items requested by a doctor. As a control technique for controlling such an analyzer, a quality control sample (control sample) whose concentration is known is periodically measured during intervals between measurements of patients/samples. If the concentration of measured data deviates from the concentration included in the control sample, the analyzer issues an alarm indicating that the data is abnormal. By measuring the control sample, it is possible to check whether or not the analyzer is abnormal on the day, to check the aging of a reagent, to judge whether or not the analyzer is sufficiently adjusted, and to judge whether or not the standard solution can be adjusted. The result of calibration, and the result of measuring the control sample, are summarized by a clinical laboratory technologist, and are then recorded and stored.

A control technique for controlling a control sample includes control performed by a clinical laboratory technologist of a hospital's clinical laboratory. Besides this technique, the multiple systems described below have already been developed and are on sale, or are implemented in public institutions.

1. Control Technique that Uses a Control Sample

Examples of a technique for distributing control samples to each hospital to control the control samples include a system that is sold by a reagent manufacturer and public institutions such as a medical association.

(1) Quality Control that Uses a Control Sample Supplied by a Reagent Manufacturer A reagent manufacturer sells, as a control sample, serum or the like whose value has already been determined to hospitals and the like. In each of the hospitals, each control samples is provided with an average value, a standard deviation used as an indicator of variations, and the like, all of which have already been determined. These values are inputted into an analyzer, or a computer used for data management in each hospital.

An automated analyzer used for clinical laboratory tests measures patients/samples to analyze items requested by a doctor. A control sample is periodically inputted during measurements of patients/samples, and thereby data is measured. If the measured data deviates from data that has already been measured, it is judged that the data is abnormal, and accordingly a check is made as to whether or not the analyzer, the reagent, the standard solution, or the like, is abnormal. A clinical laboratory technologist summarizes the measured data, and records daily fluctuations in data.

(2) In the Case where a Reagent Manufacturer Sells Control Samples, Receives Measured Results (Data) Through a Network Line, by Mail, or the Like, and Manually Summarizes the Data In the above-described method (1), there is also a system in which the reagent manufacturer supplies control samples, and collects values thereof from each individual hospital, and then summarizes the values in, for example, a service center of the reagent manufacturer. Data from the automated analyzer is not directly summarized. The results of measurements are transmitted through the network line; and data of the control samples is transmitted from a general personal computer. Data of the control samples are stored in a FD (flash disk or flexible disk), or the like. The FD is sent by mail, or the like. The results of summarizing the data are subjected to statistical processing. If a calculated value largely deviates from an average value, the measured results and the diagnostic results are sent to each hospital. Each hospital can use them as indicators of the quality control of a clinical laboratory.

(3) In the Case where Public Institutions Including a Medical Association Distribute Control Samples Public institutions including the Japan Medical Association distribute, all at once, nationwide common control samples to hospitals, clinical laboratory test centers, and the like, in Japan, about once or twice a year. The control samples which have been distributed to each of facilities by each analyzer are measured. Then, the measured results are transmitted to the Japan Medical Association so that the measured results are subjected to statistical processing. An average value and a standard deviation are calculated. Then, according to the deviation from the average value, the measured results are judged to be A (±1 SD (standard deviation), B (±2 SD), C (±3 SD), D (±4 SD). The results of the judgment are transmitted to the director of each hospital.

Besides the Japan Medical Association, the above-described method is carried out on a prefecture basis, and on a hospital group basis.

2. Control System of Analyzer

Some analyzer manufacturers for manufacturing automated analyzers, and the like, also put to practical use a system in which each analyzer manufactured by the analyzer manufacturer, which has been sold to each hospital and is located at the hospital, is connected to for example a server controlled by a service division of the analyzer manufacturer through a network line so that a state of the analyzer is remotely monitored. FIG. 1 is a diagram schematically illustrating a configuration of the whole system.

Information handled by this system includes: (1) information that is transmitted from the system of the support center to each automated analyzer; and (2) information that is transmitted from each automated analyzer to the system of the support center. In addition, the information handled by the system further includes: (3) information that is transmitted thorough the network line when each of facilities makes an inquiry to the system so as to check information controlled on the system side. Thus, the information handled by the system includes the three kinds of information.

Although there are the three kinds of information, information handling methods differ depending on analyzer manufacturers. Fore example, some analyzer manufacturers only answer a question using a network line. There are also analyzer manufacturers that support the flow of information only in one direction; more specifically, only the occurrence of an abnormal condition of an analyzer is transmitted from the analyzer to a service center.

A general example of the three kinds of information will be described as blow.

(1) Information to be Transmitted from the System of the Support Center

The support center transmits the following information:
analysis parameters for each item;
standard solution concentration for each item;
an average value, and a standard deviation, on a control sample basis (2) Information to be Transmitted from Each Automated Analyzer to the Support Center From each analyzer located in each facility such as a hospital, this system extracts basic information including: alarm information including an abnormal condition of an analyzer; the results of measuring control samples; the measured absorbance of standard solution; and the results of calibration. The above information is accumulated in an information center.

(a) alarm information including an abnormal condition of an analyzer an abnormal condition of an electric circuit, or that of a machine, which has occurred in an analyzer (b) the results of measuring control samples the results of measuring each control sample; and a reagent lot, a control sample lot, and the like (c) the results of calibration the results of measuring standard solution (a) measured data the measured absorbance of each standard solution (dominant wavelength, secondary wavelength)

the initial absorbance (b) calculation parameter

K factor

S1ABS (3) Data Summarizing Method of a Data Center

The information center summarizes data of control samples on a facility basis to compare average values, and summarizes standard deviation information.

summarization on a facility basis an average value between-run reproducibility a standard deviation An inquiry about the data and the information is responded by use of a network line. For example, if the alienation of data is extraordinarily large, a comment about an improvement method, or the like, is transmitted. In addition, if it is not possible to understand how to handle an analyzer, services including a response to an inquiry are also provided. The results of controlling the standard solution are illustrated with a graph.

A technology relating to the above, for example which is described in patent document 1 (WO 02/052278A1), has been applied for a patent.

SUMMARY OF THE INVENTION

The above-described existing technologies are presented and implemented by reagent manufacturers, analyzer manufacturers, public institutions, and the like. Unfortunately, one system does not cover all of clinical laboratory tests. The analyzer manufacturers give higher priority to the control of analyzers, whereas the reagent manufacturers give higher priority to sales of control samples, and the control of reagents. In the case of the public institutions, a system is operated once a year. Accordingly, from the viewpoint of daily inspection, the system does not substantially function as a quality control system or a support system. On the other hand, from the viewpoint of clinical laboratory tests, in the major economic trend represented by the reduction in medical costs, it becomes necessary to ensure the worldwide data compatibility, and also to ensure the reliability of medical treatment, both of which are problems to be solved.

1. Ensuring of the Worldwide Data Compatibility

In clinical laboratory tests, for regular calibration of an analyzer and reagents, a standard solution is measured. In many cases, however, each reagent manufacturer makes their standard solution according to their own prescriptions. Accordingly, the results of calibration do not become the same depending on which standard solution is used. In addition, even in the case of a measurement reagent for the same item, there may be a difference between measurement principles. Therefore, when an enzyme method is used, even if control samples are measured with the same standard solution, different values are obtained depending on a kind of enzyme or the concentration. To be more specific, it is important to keep track of what kind of standard solution used by a clinical laboratory of each hospital to perform calibration. If measurement principles of measuring reagents differ from each other, or if standard-solution manufacturers differ from each other, the comparison between measurements is meaningless.

On the other hand, not all patients complete medical treatment in one hospital. It is becoming commonplace to change to another hospital a plurality of times depending on a kind of illness. However, if standard solutions differ on a hospital basis, even if blood collected from the same patient is analyzed, acquired data differs. Therefore, measurements are wastefully repeated many times in order to check data. If inspection data differs, patients also distrust a doctor and a hospital.

It is also important for each hospital to know whether or not data acquired in the hospital is compatible with that of other hospitals.

Moreover, also when a medicine manufacturer checks the results of treatment to announce it in the academic society, there has been a major problem that the data compatibility is not reliable.

2. Ensuring of the Reliability of Medical Treatment (the Control of Clinical Laboratory Relating to ISO15189)

Also from the viewpoint of ensuring the trustworthiness from patients, it is becoming important for medical institutions including hospitals to record that inspection data of each patient has been acquired under fixed conditions. In particular, it is indispensable that inspection data and inspection conditions are daily recorded on the basis of global standards such as ISO15189, judgments by hospital evaluation institutions, and the like. Although it is natural that patient charts, electronic patient charts, and the like, are recorded as patient data, recording and storing measurement conditions of an analyzer require the enormous amount of effort. The inspection conditions include: the results of calibration on an item basis; a reagent lot; whether or not aging of a reagent has occurred; whether or not a standard solution lot has been changed; and a judgment of the results of calibration. Thus, daily recording of information about several tens of items is required.

Recently, the number of laboratory technologists has been reduced to the required minimum as a result of improving the efficiency of a clinical laboratory. Thus, it is difficult for the clinical laboratory technologists to manage the enormous amount of information printed on paper.

In addition, it is very important to check whether or not data which has been daily reported by a clinical laboratory is stable. Especially, it is important that the check can be made in real time. Even if data is printed on paper, it is difficult to retroactively check the data. Control systems for controlling control samples, which are sold by reagent manufacturers, do not control the results of calibration for a standard solution, etc. Therefore, it has been difficult to control both the control samples and the results of calibration in a system. Such a system was insufficient as a control system.

In addition, Japanese Patent Application Laid-Open No. 2003-4750 discloses a method in which quality control data is checked through a dedicated line as checking means for checking daily used data. This technique is a publicly known example.

As described above, there was has been means for checking, in real time, whether or not data which is used for daily inspection is correct.

The quality control system according to the present invention transmits, in real time, results of calibration performed by a clinical laboratory of each hospital; results of measuring a quality control material; reagent lot numbers; standard solution numbers; and quality control material lot numbers; to a support center through network lines. The reagent lot numbers, standard solution numbers, and quality control material lot numbers are used for the measurements. In addition, the quality control system transmits, which are used for the measurements. The support center summarizes the results of calibration, and data of the quality control material. The summarized data is subjected to statistical processing to check changes from the previous day, and to check reagent data. A clinical laboratory of each hospital makes an access to the support center through the network line to check the status of an analyzer.

A reagent manufacturer and an analyzer manufacturer provide the support center with not only reagent lot numbers, but also allowable values including average values of the standard solution and the control samples, and standard deviations thereof, on a lot basis and on an item basis. The support center transmits the information to an analyzer of each hospital through the network lines. In addition, the information is utilized as a base of the statistical processing in the support center.

The statistical processing is performed to process data that changes with time and is obtained from a single facility. Furthermore, the statistical processing is performed with results of measuring the same control sample lot and the same standard solution on an item basis, the results being extracted from among data in a plurality of facilities. Then, the statistical processing also calculates quality control data, and distribution information including average and deviation values of the results of calibration. When processed data of each hospital is displayed, statistical data of the plurality of facilities, and the average and deviation values, are also displayed on an item basis.

If the support center performs the quality control of control samples and the control of the calibration results, each hospital can obtain two kinds of effects as follows:

1. Release from the Control

Control samples in the past and calibration results are summarized together with reagent lot numbers, standard solution lot numbers, and control sample lot numbers. The summarized data is then recorded. In particular, because the support center performs statistical processing of the calibration results, it is possible to largely reduce a workload of each hospital. Moreover, if an inquiry is made to the support center, information about standard solution and control samples can be displayed in combination. Accordingly, it is possible to make a check in real time. This makes it possible to considerably reduce the data retrieval time.

Also from the viewpoint of the standards relating to the quality control of a laboratory, such as ISO15189, information about reagents, standard solution, and control samples corresponding to all analyses are stored. As a result, the control is facilitated.

2. Checking of the Difference Between Data, and Data Unification

Because data is checked in a support center, the difference between analyzers, the difference between reagent manufacturers, and the difference between reagent prescriptions are clear. On the other hand, if measurements are made under the same reagent conditions, the difference between data of one facility and that of the other facilities becomes clear. Therefore, the data unification becomes possible.

DETAILED DESCRIPTION OF THE PREFERRED EMBODIMENTS

Figure 1:
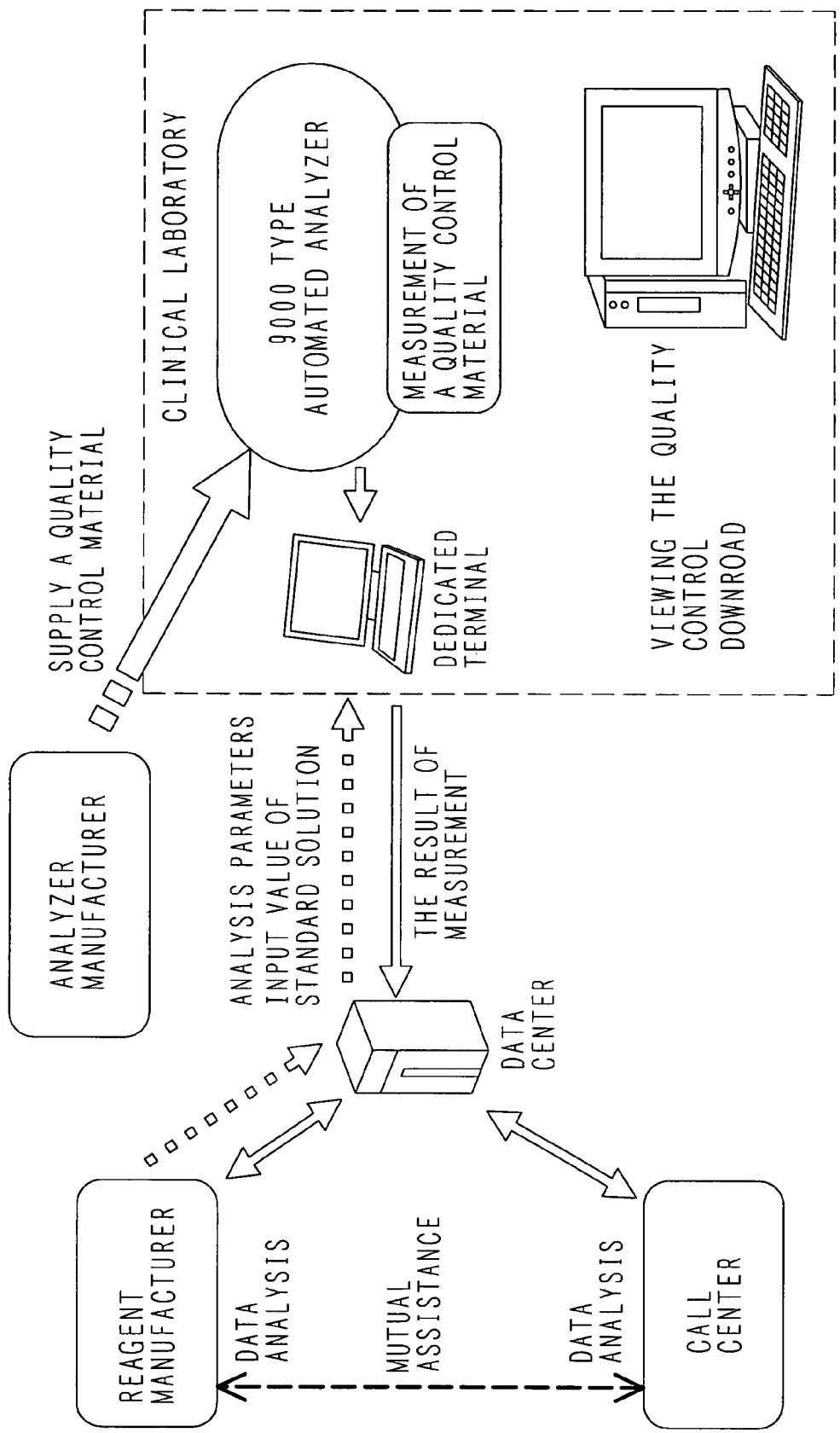
FIG. 1 is a diagram schematically illustrating a system.

The present invention will be specifically described with respect to embodiments as below.

First Embodiment

A system according to the present invention includes analyzers that are located in each hospital; and a repeater or a personal computer that is disposed to connect each of the analyzers with a support center through network lines.

The following information is mutually transmitted and received among these systems:
(a) Parameters;
   a code number, and analysis parameters, on an item basis;
   a lot number of standard solution, and the concentration, on an item basis; and
   a lot number of a control sample, and the concentration, on an item basis;
(b) Information about each analyzer;
   content of an alarm occurred in an analyzer, and the number of times the alarms have occurred;
   the result of measuring a standard solution;
   the result of measuring a control sample
(c) The result of statistical processing;
   the results of calibration for each item;
   the initial absorbance, an average value of sensitivity, and a standard deviation, on an item basis;
   lot fluctuations of a reagent; and
   quality control information;
   an average value, and a standard deviation, on a control sample basis.

1. Analyzer

The analyzer operates as described below.

(1) Operation of an Analyzing Unit

As described below, the analyzing unit operates in order of sampling, divided injection of reagents, stirring, photometric measurements, cleaning of a reaction container, and data processing such as the conversion of concentration.

A plurality of sample containers each containing a sample are placed on a rack. The rack is controlled by a computer through an interface.

In addition, the rack is moved to the bottom of the sample divided-injection probe according to the order of samples to be analyzed. The specified amount of sample contained in the specified sample container is injected into the reaction container in a divided manner by the sample pump that is connected to a sample divided-injection mechanism.

The reaction container into which the sample has been injected in a divided manner is moved to a first reagent adding position in a reaction vessel. By use of a reagent pump that is connected to a reagent divided-injection probe, the specified amount of reagent which is absorbed from a reagent container is added to the reaction container that has been moved. A bar code reader is attached to a reagent bottle. The bar code reader reads out a bar code label so as to acquire information about where the reagent container is placed and information about which item of the reagent is set in the reagent container.

After the first reagent is added to the reaction container, the reaction container is moved to a position of a stirring mechanism where first stirring is performed.

Such addition and stirring of the reagent are performed for the first reagent to a fourth reagent.

The reaction container in which the contents have been stirred passes through luminous flux emitted from a light source. The absorbance at this point of time is detected by a multiwavelength photometer. The detected absorbance signal passes through an A/D converter, and is input into the computer through the interface. The absorbance signal is converted into data on the concentration of the sample in the computer.

The converted concentration data is printed by a printer through the interface, and is also displayed on a screen.

After a reaction solution included in the reaction container has been measured and subjected to photometric measurement, the reaction container is moved to the position of a cleaning mechanism. Then, the contents of the reaction container are discharged by a container cleaning pump. After that, the reaction container is cleaned with water, and is then subjected to the next analysis.

In the case of analyzers adopting a rack method, a sample rack can be identified for the use of standard solution, a control sample, and general samples. In addition, in the case of sample disk type analyzers, there is an area for setting a control sample and standard solution at a position at which a sample on a disk is set. In the above two cases, a bar code label is attached to each of these samples. A bar code reader reads out the bar code label so that identification is performed. After the reading, the analyzer executes calibration, and performs measurements of the control sample, according to information.

(2) Identification of Information

Identification information is added to the reagent container, the standard solution, and the control sample so that identification is performed on an item basis. On the basis of the information, the analyzer and the system perform the management of the whole information.

Reagent container

Identification information used to identify information on an item basis (in general, a bar code label) is attached to each reagent container. Each reagent bar code includes the following information:
  an item code
  a lot number
  an expiration date Standard solution Identification information used to identify information on an item basis (in general, a bar code label) is attached to the standard solution. Each reagent bar code includes the following information:
  standard solution code
  a lot number
  an expiration date Control sample Identification information used to identify information on an item basis (in general, a bar code label) is attached to each control sample. Each reagent bar code includes the following information:
  a control sample code
  a lot number
  an expiration date (3) Downloading of Parameters There are three kinds of parameters that are transmitted from a network through a repeater: analysis parameters including the amount of sample, and the amount of reagent, which are required for analysis on an item basis; parameters relating to standard solution; and parameters relating to a control sample.

Analysis-parameter version information for each item
  an item code, the amount of a sample, the amount of a reagent, the wavelength, an analysis method (the rate analysis, the endpoint analysis, or the like), and the reaction time
  Standard solution parameters
  a standard solution code
  a lot number
  an item code, and the concentration of standard solution, on an item basis
  Control sample parameters
  a control sample code
  a lot number
  an item code, and the concentration of a control sample, on an item basis
  Download method An operation unit of the analyzer issues an instruction to download a required analysis item and parameters thereof through a repeater. The repeater transmits specified parameters included in the parameters which have already been transmitted from the support center and have been stored in a memory.

The analysis parameters, the standard solution parameters, and the control sample parameters are stored in the analyzer, and the three types of the parameters are mutually associated with one another by each item code. Identification information is added to the reagent, the standard solution, and the control sample that are actually set in the analyzer. The identification information is in general authenticated by use of a bar code label.

(4) Execution of Calibration

The calibration is performed in the above-described analyzer. More specifically, two kinds of solution (blank solution and standard solution, which are origins) are set in the analyzer, and then analysis is performed twice for each sample.

The result of the calibration is the absorbance as a result of reaction.

The absorbance of the dominant wavelength, and that of the secondary wavelength, which are measured by the reaction of the blank solution and the standard solution The absorbance of the dominant wavelength, and that of the secondary wavelength, are set on an item basis; and they differ depending on absorbance spectrum of the reaction solution.

Calculation process—a calibration curve of the reaction is calculated from the blank solution and the standard solution

[Calculation of S1ABS]

An origin is determined from the blank solution. The blank absorbance S1ABS is calculated from an average value of the blank solution measured twice.

[Calculation of K Factor]

A tilt of the calibration curve is determined from the blank solution and the standard solution. In general, the following equation is used:

[(the absorbance of the standard solution)−(the absorbance of the blank solution)]/[(the concentration of the standard solution)−(the concentration of the blank solution)]

The absorbance of the standard solution and the absorbance of the blank solution are based on an average value obtained by making measurements twice.

In general, measurements of the blank solution and the standard solution are made twice or three times in many cases. If the reaction is unstable, the measurements are often made three times or more so as to increase the quality (precision).

In addition, there is a case where a multipoint calibration curve obtained by use of two or more kinds of standard solution is also used. An approximated curve is used for the calculation of the calibration curve.

(5) Execution of Quality Control

In order to monitor the state of a reagent and that of an analyzer during measurements of patients/subjects, it is necessary to measure a control sample, whose concentration is known, for each fixed number of patients/subjects. In general, this is called quality control. In the case of the control sample, it is known that an approximate value of the concentration and an approximate activity value of each item are added. These values are transmitted from the system.

2. Repeater

Each repeater includes the following functions:

(1) A function of receiving parameters from the support center to store the parameters, and transmitting the parameters in response to a request from the analyzer;

Parameter information is received from the support center, and is then stored in the repeater. A plurality of pieces of information corresponding to each parameter, including version information and a lot number, are stored even if the parameter is included in the same item. Because the analyzer does not require all lot numbers, parameters are transmitted to the analyzer according to information about a reagent, standard solution, and a control sample that have actually been set in the analyzer.

Analysis parameter of each item
    version information; and
    an item code, the amount of sample, the amount of reagent, the wavelength, an analysis method (the rate analysis, the endpoint analysis, or the like), and the reaction time
    Standard solution parameters
    a standard solution code;
    a lot number; and
    an item code, and the concentration of standard solution, on an item basis
    Control sample parameters
    a control sample code;
    a lot number; and
    an item code, and the concentration of a control sample, on an item basis (2) A function of receiving information from an analyzer, and then transmitting the information to the support center;

The analyzer transmits an analyzer alarm, the result of measuring the standard solution, and the result of measuring the control sample.

descriptions of alarms occurred in the analyzer, and the number of times the alarms have occurred;
    an alarm code number of each alarm occurred in the analyzer, and the number of times the alarm have occurred; and
    the time of occurrence
    the result of measuring the standard solution;

On an item basis, a lot number of the standard solution, and a lot number of the reagent, which have been used for the measurements, are transmitted together with the following information:
[the absorbance of the dominant wavelength, and that of the secondary wavelength, which are measured by the reaction of the blank solution and the standard solution];
[Calculation of S1ABS]; and
[K factor]
    the result of measuring the control sample A lot number of the standard solution, and a lot number of the reagent, which have been measured for each item, are transmitted together with the following information:
[the result of measurements]; and
[the date and time of measurements]

3. Support Center

A system of the support center has two main functions as described below:

(1) A Function of Transmitting Parameters from Each Hospital to a Repeater Used for an Analyzer;

The support center has a transmission function of transmitting analysis parameters, standard solution parameters, and control sample parameters on an analysis item basis, the parameters being registered by a reagent manufacturer.

(2) A Function of Collecting Information from a Repeater of an Analyzer;

In the support center, all of the information of each analyzer received from each hospital is stored for each hospital.
    descriptions of alarms occurred in the analyzer
    the number of times the alarms have occurred
    an alarm code number of each alarm occurred in the analyzer
    the number of times the alarm have occurred
    the time of occurrence
    the result of measuring the standard solution;

On an item basis, a lot number of the standard solution, and a lot number of the reagent, which have been used for the measurements, are transmitted together with the following information:
[the absorbance of the dominant wavelength, and that of the secondary wavelength, which are measured by the reaction of the blank solution and the standard solution];
[Calculation of S1ABS]; and
[K factor]
    the result of measuring the control sample (3) A Statistical Processing Function;

In the support center, statistical processing is performed on a hospital basis, and then an average value of the standard solution, and a standard deviation thereof, are calculated on an item basis.
    calculation on a hospital basis An average value and a standard deviation are calculated from measured values acquired by measuring the standard solution ten times or more in the past. A value equivalent to three times the standard deviation is defined as an allowable limit, which is expressed as ±3 SD with respect to the average value.

Statistical processing that uses a plurality of hospitals

If the same reagent lot and the same standard solution lot are used in a plurality of hospitals, average and standard deviation values of all of the hospitals are estimated from those of each hospital.

(4) A Function of Displaying the Results of Measurements

Figure 2:
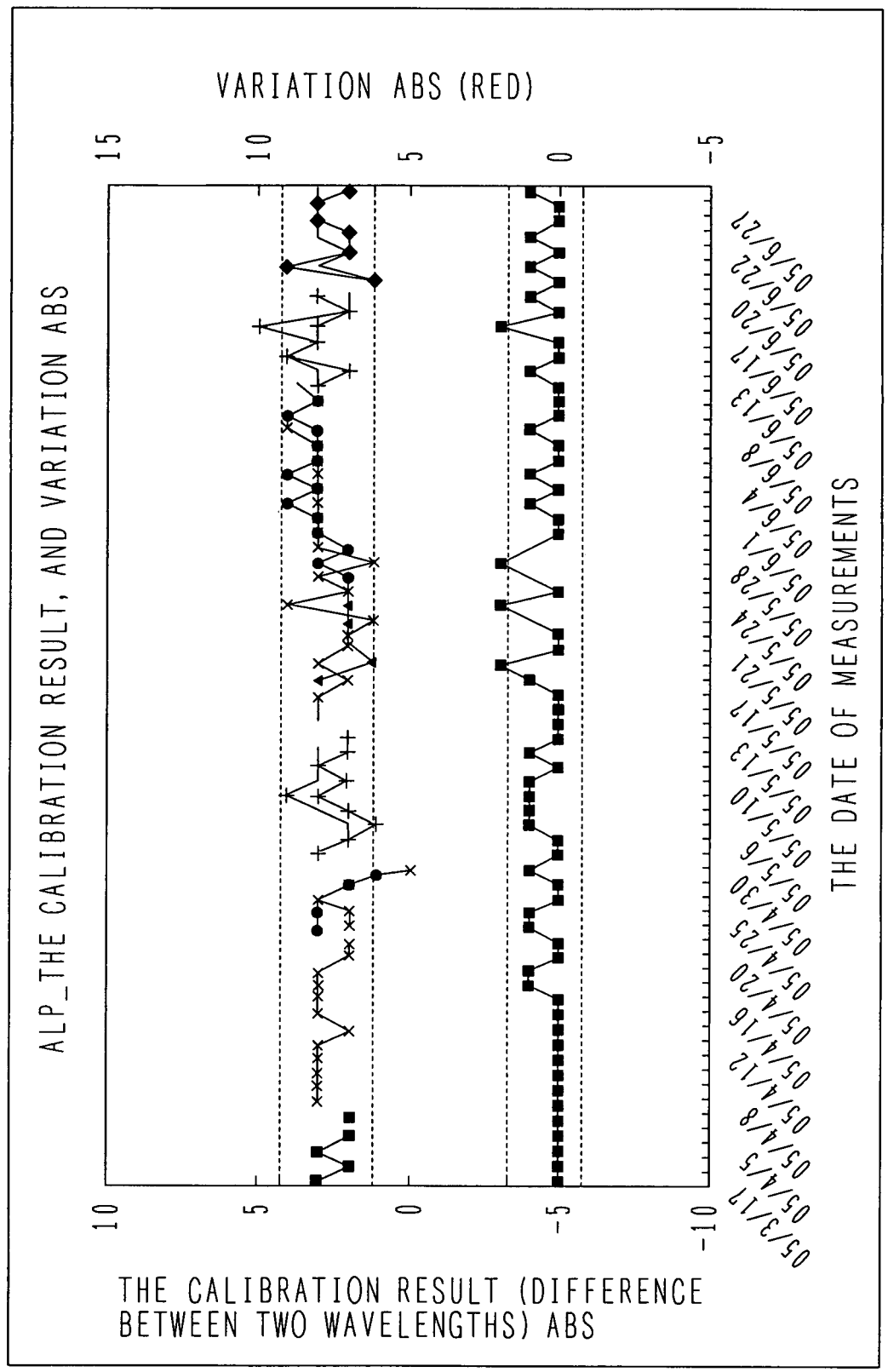
FIG. 2 is a chart illustrating the quality control of the results of ALP calibration.
Figure 3:
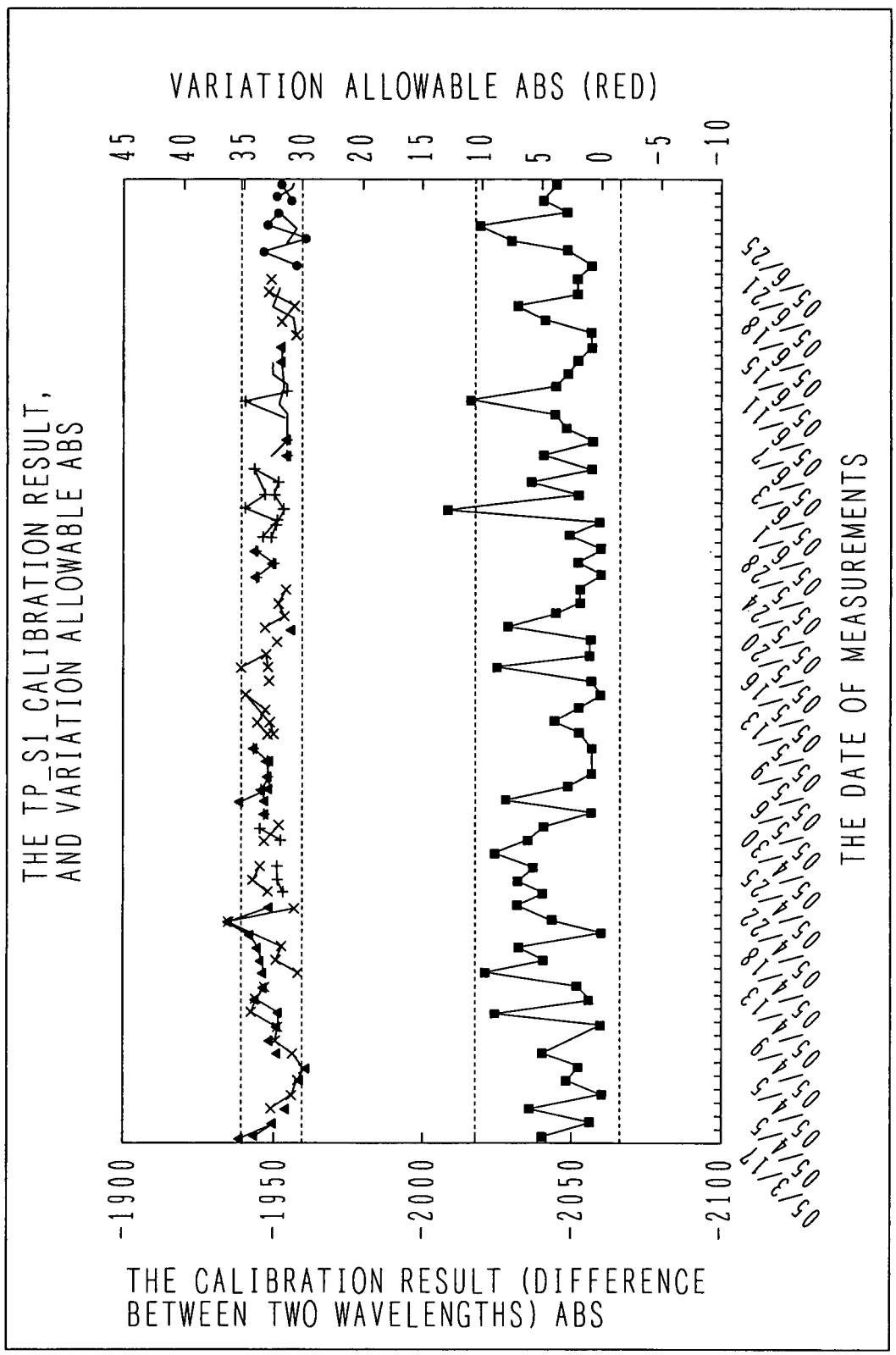
FIG. 3 is a chart illustrating the quality control of the results of TP calibration.

The display function of displaying each item includes:
    (a) Displaying Information about Only the Standard Solution;
    the results of measuring the standard solution are displayed with the dominant wavelength and the secondary wavelength;

the results of measuring the standard solution are displayed with the deference between the dominant wavelength and the secondary wavelength control values are calculated from average and standard deviation values acquired as a result of the statistical processing, and then the control values are displayed FIGS. 2, 3 are charts each illustrating an example of the results of calibration and the allowable width determined from the calculated average and standard deviation values. In facilities operating every day, it is possible to use this control width to check whether or not a calibration problem has occurred on the day.

(b) Superimposed Display

Figure 4:
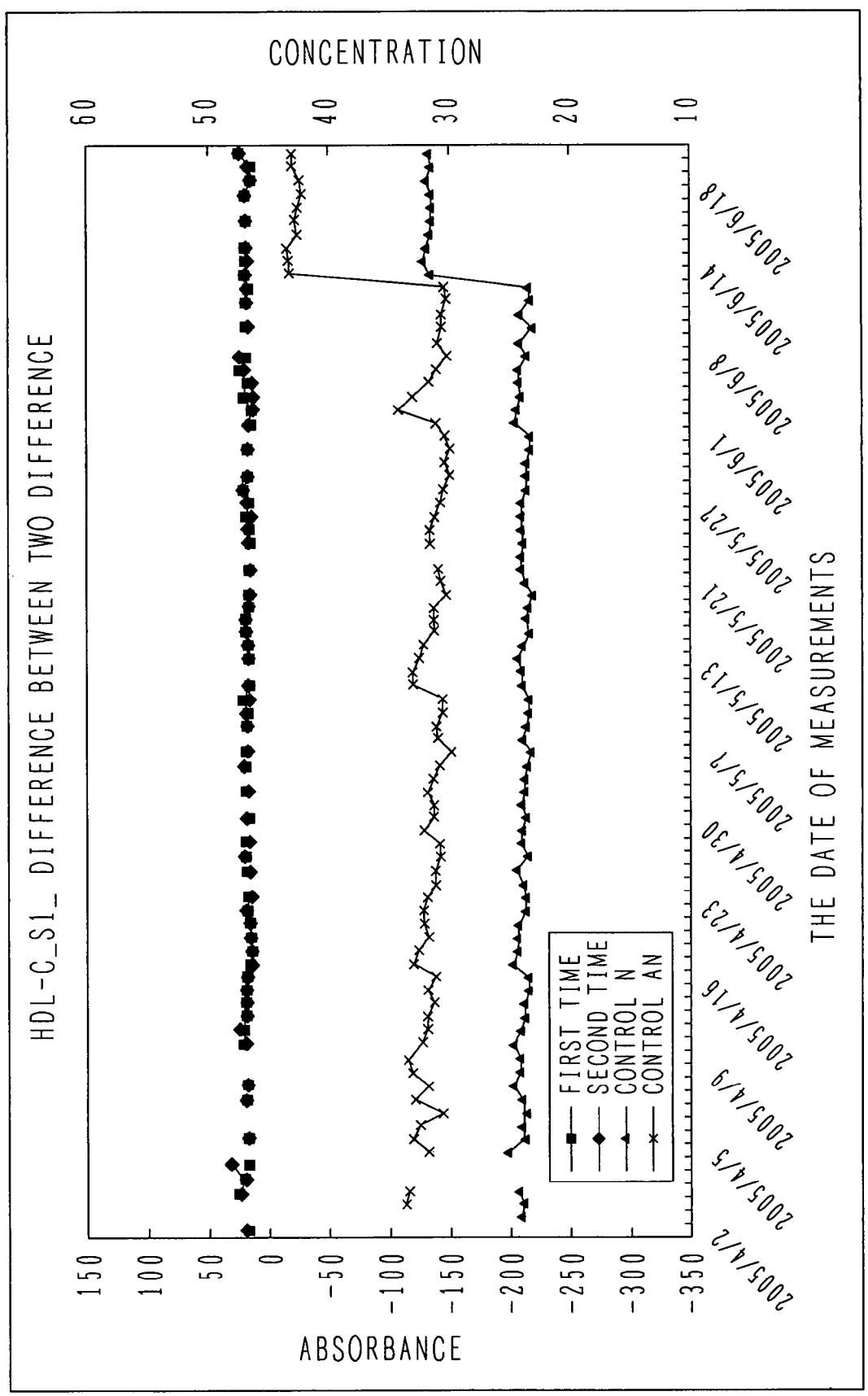
FIG. 4 is a chart illustrating the results of calibration and quality control information in combination.
Figure 5:
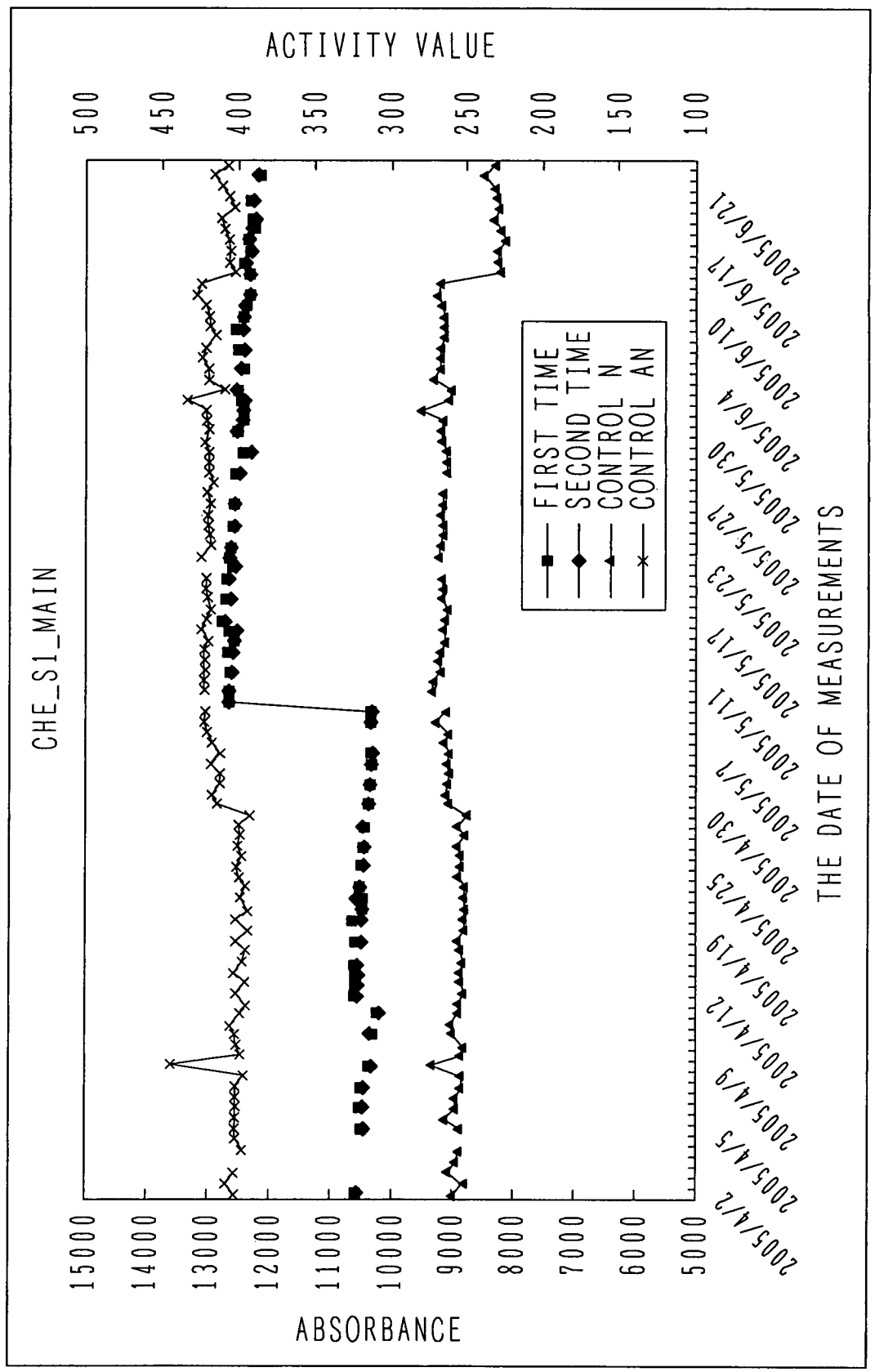
FIG. 5 is a chart illustrating the quality control with respect to changes of reagent lots.

The results of measuring a plurality of control samples are superimposed on each piece of information about the standard solution of (a).

the results of measuring the standard solution, and the results of measuring a plurality of control samples are displayed FIGS. 4, 5 are charts each illustrating the blank absorbance of the standard solution and the results of measuring a control sample. FIG. 4 illustrates a state in which a control sample lot has changed. It is possible to fully understand from FIG. 4 how a control sample has changed. Referring to FIG. 5, the reagent lots are changed. However, the results of calibration and measured data of the control sample have not largely changed. Accordingly, it is found out that there has been no influence of the change of the reagent lot.

(c) Displaying Comments

The information display screens of (a) and (b) display a difference between the reagent lots, a difference between the reagent bottles, a difference between the standard solution lots, and a difference between the control sample lots. There are several kinds of displaying methods including: displaying each lot with different color; and displaying lot numbers on the screen.

Figure 6:
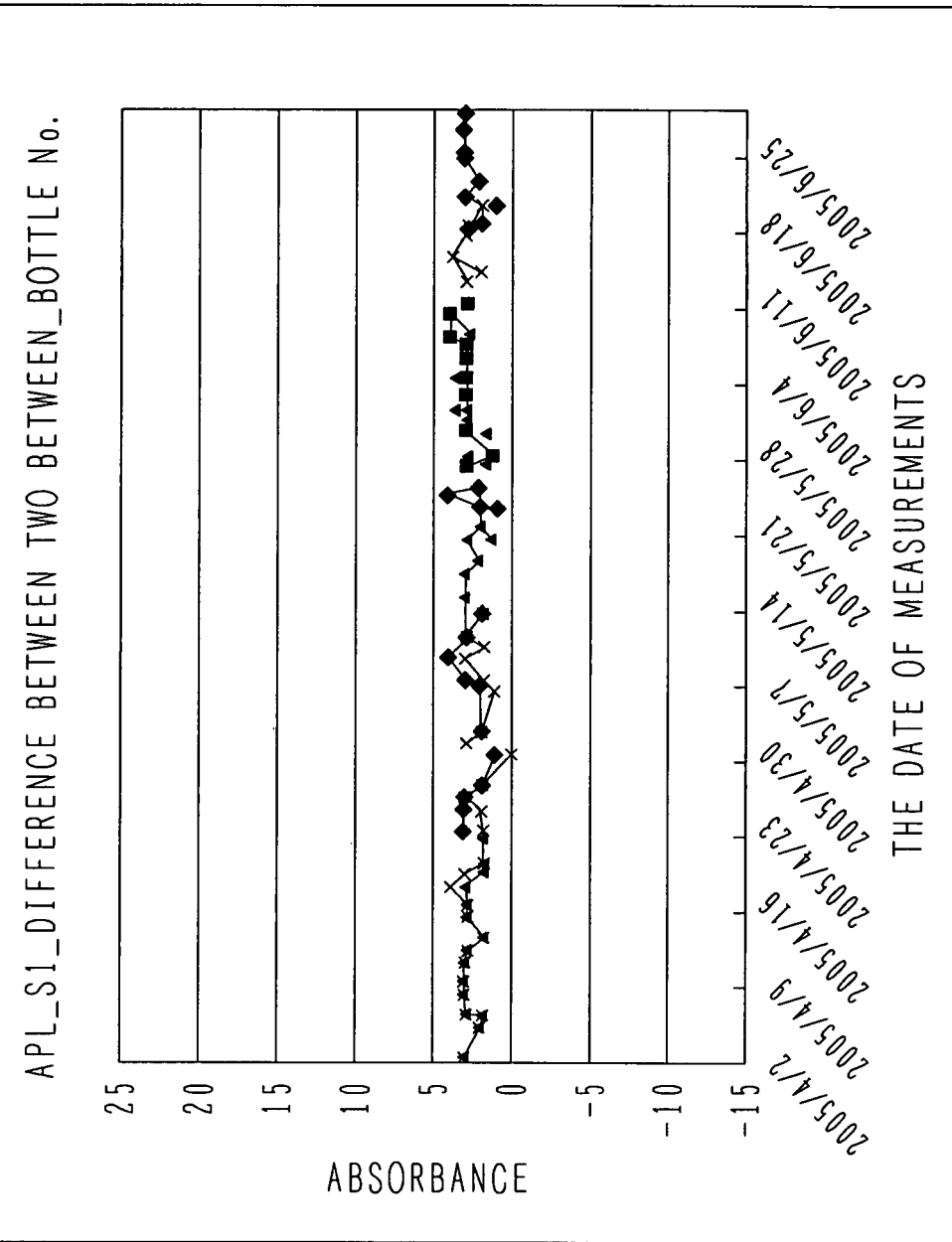
FIG. 6 is a chart illustrating the control of the calibration results on a reagent bottle basis (difference between dominant and secondary wavelengths)
Figure 7:
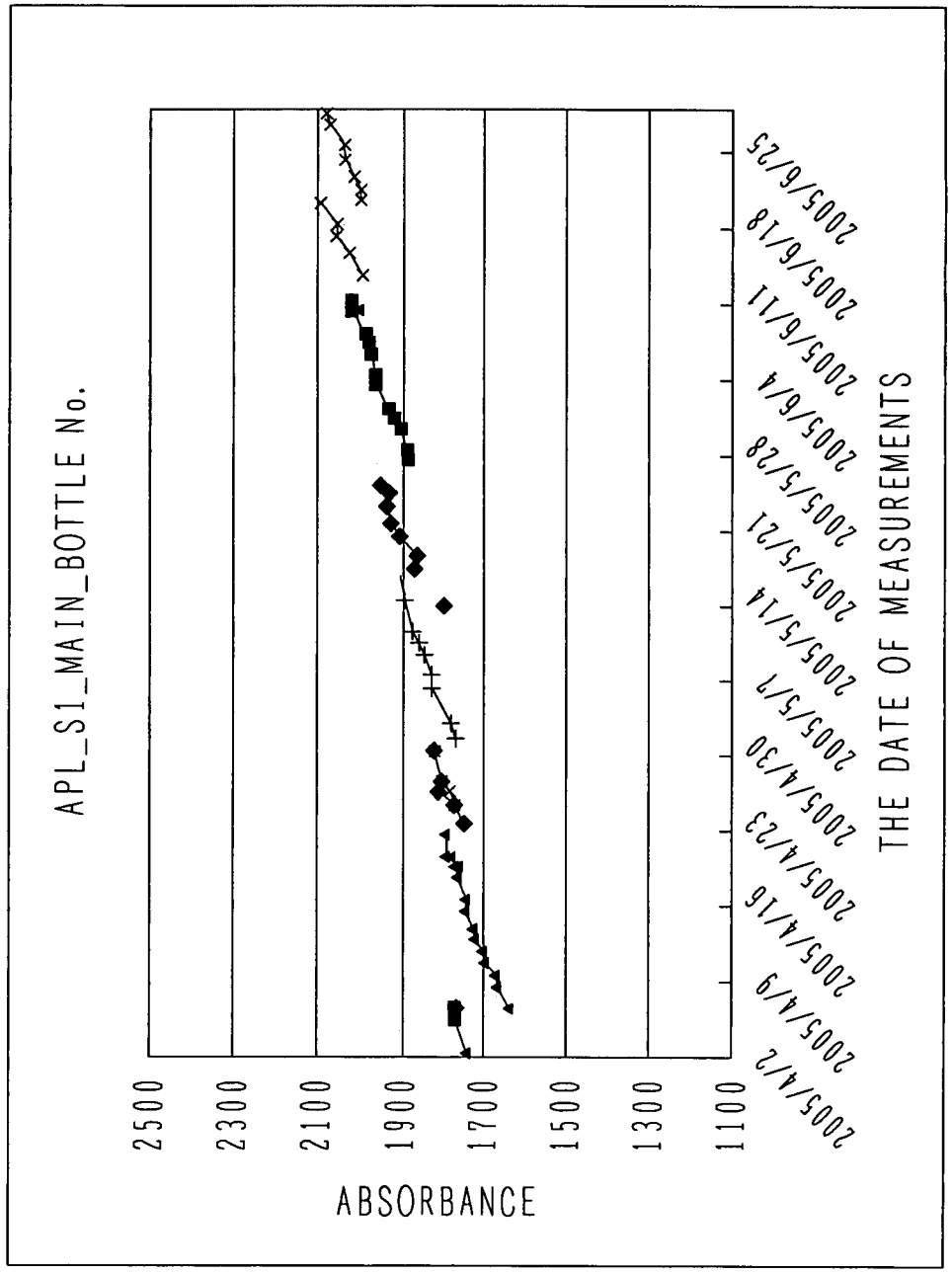
FIG. 7 is a chart illustrating the control of a reagent bottle basis (dominant and secondary wavelengths).

FIGS. 6, 7 are charts each illustrating an example of ALP measurements. The difference between the two wavelengths shown in FIG. 6 is not clear with respect to changes of the state of each solution contained in each reagent bottle. However, it is possible to clearly observe changes of each reagent bottle and those of each reagent lot, based on the dominant/secondary wavelengths shown in FIG. 7.

(d) Displaying a Comparison with Other Hospitals

In the case of the information display screen of (a) and (b), if the same reagent lot and the same standard solution lot are used in a plurality of hospitals, each of which is connected to the support center, an average value, and the distribution, of these facilities are displayed on a standard solution screen. There are several kinds of displaying methods including: displaying each lot with different color; and displaying lot numbers on the screen.

(5) Method of Making an Inquiry to the Support Center from a Clinical Laboratory in Each Hospital When an inquiry about data is made from each hospital, the inquiry is made to a website of the support center through a network line. A password and a hospital code, which are required to make an access, are distributed to each hospital from the support center in advance. When an access is made, a person in charge of each hospital can extract only information of the hospital in question from each screen.

By use of a system and an analyzer to which the present invention is applied, it is possible to determine control values from all of the analyzers, reagents, standard solutions, and control samples, and thereby to maintain clinical laboratory tests with high reliability.

Second Embodiment

A configuration of an analyzer is the same as that of the first embodiment. In a system, the analyzer includes a signal line associated with a repeater, and a memory. The repeater only functions as a memory for data communications. Therefore, the substitution becomes possible by incorporating the repeater into the analyzer. This avoids the necessity for separately providing a repeater and creates an empty space.

Third Embodiment

An example of a system configuration is the same as that of the first embodiment. For a function of statistical processing, a method of calculating the concentration of standard solution, which has been established in ISO15189, is adopted. This is a clinical laboratory test system for calculating uncertainty of standard solution by using the standard solution a plurality of times.

This enables the support center to calculate the uncertainty required for each standard solution lot. As a result, the amount of operations required for each clinical laboratory is largely reduced.

What is claimed is:

1. A quality control system comprising:
a plurality of medical facilities, each of which includes an automated analyzer for mixing a reagent with a sample to analyze a target component contained in the sample;
a dedicated terminal connected to said automated analyzer at each facility;
a first communication network connected to each dedicated terminal at each facility;
collection means for collecting information about analysis parameters including a lot number of a standard solution used for calibration and a lot number of a standard solution used for quality control, and information about results of measuring the standard solution used for quality control and results of measuring the standard solution used for calibration, from each facility;
a second communication network line connecting said collection means with said terminal of each facility for receiving and transmitting information;
database storing means for storing the information collected by the collection means from each facility;
a communication network line connecting said database storing means to said collection means for receiving and transmitting information;
statistical-processing calculation means for calculating average and standard deviation values of measuring results of a standard solution used for calibration in the same standard solution lot, based on the information about analysis parameters including information of lot number of the standard solution used for calibration for each facility stored in said database storing means, and the information about the results of measuring the standard solution used for calibration for each facility stored in said database storing means; and
information supplying means for supplying at least one of said average and standard deviation values calculated by said statistical-processing calculation means to the facility which includes the automated analyzer that measured the same standard solution of the same lot number used for calibration.

2. The quality control system according to claim 1, wherein:
a support center including the statistical-processing calculation means includes means for reporting the calculation results obtained by the statistical-processing to each facility.

3. The quality control system according to claim 2, further comprising
   means for using the statistical-processing calculation means to calculate, for each facility, upper and lower limits for the measurement sensitivity and the blank absorbance of a reagent, the measurement sensitivity and the blank absorbance being measured on a daily basis for each item to be analyzed, and for transmitting, if the calibration results of each analyzer go out of a range between the upper and lower limits, information to each facility through a communication network line.

4. The quality control system according to claim 2, further comprising
   means for simultaneously displaying for each item to be analyzed, control values of the calibration having been subjected to the statistical processing in the support center and result of measuring a quality control sample on a screen of the automated analyzer of each facility.

5. The quality control system according to claim 4, further comprising
   means for identifying and displaying, if the standard solution lot or the reagent lot is changed, the changed lot on the screen.

6. The quality control system according to claim 2, further comprising
   means for calculating an allowable value of a K factor from results of calibration performed a plurality of times, and for, if the allowable value exceeds ±2 SD, issuing an alarm through a communication network line.

7. The quality control system according to claim 1, wherein:
   as the result of calibration, a dominant wavelength and a secondary wavelength with respect to the blank absorbance of the reagent are separately displayed.

8. The quality control system according to claim 1, further comprising
   means for changing for each item to be analyzed, a displayed color for calibration for each reagent bottle.

9. The quality control system according to claim 8, further comprising:
   storing means for storing for each item to be analyzed, a pattern of change with time of the absorbance for each reagent bottle; and
   means for making a comparison with the pattern for each reagent bottle, and for, if there is a difference from the pattern of change with time, issuing an alarm for an abnormal condition through a communication network line.

10. The quality control system according to claim 9, further comprising
    means for extracting for each item to be analyzed, the result of measuring the same control sample lot and the same standard solution from a plurality of facilities so that the measurement result is subjected to statistical processing, and for displaying quality control data, and distribution information, including average and deviation values of the calibration result.

11. The quality control system according to claim 1, further comprising
    means for, if the same reagent lot and the same standard solution lot are used, calculating a standard deviation and an average value from absorbance data that has been collected as a result of performing measurement ten times or more in the past, and then storing the standard deviation and the average value as control coefficients, the calculation being performed for each calibration.

12. The quality control system according to claim 11, further comprising
    means for, if the same reagent lot and the same standard solution lot are used, calculating uncertainty obtained from calibration data that has been collected as a result of performing calibration ten times or more in the past.

13. The quality control system according to claim 1, further comprising means for displaying, on a screen, information together with quality control data of control samples,
    wherein quality control data, and the calibration result, of a plurality of other facilities are displayed.

14. A quality control method for a system which includes a plurality of medical facilities, each of which includes an automated analyzer for mixing a reagent with a sample to analyze a target component contained in the sample, and a dedicated terminal connected to said automated analyzer at each facility; the method comprising:
    collecting information about analysis parameters including a lot number of a standard solution used for calibration and a lot number of a standard solution used for quality control, and information about results of measuring the standard solution used for quality control and results of measuring the standard solution used for calibration, from each facility;
    storing the information collected from each facility; and
    calculating average and standard deviation values of measuring results of a standard solution used for calibration in the same standard solution lot, based on the information about analysis parameters including the stored information of lot number of the standard solution used for calibration for each facility, and the stored information about the results of measuring the standard solution used for calibration for each facility; and
    supplying at least one of said average and standard deviation values to the facility which includes the automated analyzer that measured the same standard solution of the same lot number used for calibration.

15. The quality control method according to claim 14, further comprising:
    calculating, for each facility, upper and lower limits for the measurement sensitivity and the blank absorbance of a reagent, the measurement sensitivity and the blank absorbance being measured on a daily basis for each item to be analyzed; and
    transmitting, if the calibration results of each analyzer go out of a range between the upper and lower limits, information to each facility.

16. The quality control method according to claim 14, further comprising:
    if the same reagent lot and the same standard solution lot are used, calculating a standard deviation and an average value from absorbance data that has been collected as a result of performing measurement ten times or more in the past, and then storing the standard deviation and the average value as control coefficients, the calculation being performed for each calibration.

17. The quality control method according to claim 16, further comprising
    if the same reagent lot and the same standard solution lot are used, calculating uncertainty obtained from calibration data that has been collected as a result of performing calibration ten times or more in the past.

18. The quality control method according to claim 14, further comprising:
    calculating an allowable value of a K factor from results of calibration performed a plurality of times, and
    if the allowable value exceeds ±2 SD, issuing an alarm.

19. The quality control method according to claim 18, further comprising:

changing, for each item to be analyzed, a displayed color for calibration for each reagent bottle;

storing for each item to be analyzed, a pattern of change with time of the absorbance for each reagent bottle; and making a comparison with the pattern for each reagent bottle and, if there is a difference from the pattern of change with time, issuing an alarm for an abnormal condition.

20. The quality control method according to claim 19, further comprising:

extracting for each item to be analyzed, the result of measuring the same control sample lot and the same standard solution from a plurality of facilities so that the measurement result is subjected to statistical processing, and displaying quality control data, and distribution information, including average and deviation values of the calibration result.

* * * * *